United States Patent
White

(10) Patent No.: US 12,133,770 B2
(45) Date of Patent: *Nov. 5, 2024

(54) ULTRASOUND SYSTEM WITH AUTOMATED WALL TRACING

(71) Applicant: FUJIFILM SONOSITE, INC., Bothell, WA (US)

(72) Inventor: Christopher A. White, North Vancouver (CA)

(73) Assignee: FUJIFILM SonoSite, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/155,171

(22) Filed: Jan. 17, 2023

(65) Prior Publication Data

US 2023/0148997 A1     May 18, 2023

Related U.S. Application Data

(63) Continuation of application No. 15/974,255, filed on May 8, 2018, now Pat. No. 11,553,900.

(51) Int. Cl.
    *A61B 8/08*     (2006.01)
    *A61B 8/00*     (2006.01)
    (Continued)

(52) U.S. Cl.
    CPC ............ *A61B 8/5223* (2013.01); *A61B 8/065* (2013.01); *A61B 8/14* (2013.01); *A61B 8/463* (2013.01);
    (Continued)

(58) Field of Classification Search
    CPC ......... A61B 8/5223; A61B 8/065; A61B 8/14; A61B 8/463; A61B 8/5261; A61B 8/5276; A61B 8/5284; A61B 8/5292; A61B 8/0883; A61B 8/06; A61B 8/0891; A61B 8/486; G16H 50/30
See application file for complete search history.

(56) References Cited

U.S. PATENT DOCUMENTS

| | | |
|---|---|---|
| 11,553,900 B2 | 1/2023 | White |
| 2004/0247165 A1 | 12/2004 | Nishiura |

(Continued)

FOREIGN PATENT DOCUMENTS

| | | |
|---|---|---|
| CN | 106388832 A | 2/2017 |
| JP | 11-128227 A | 5/1999 |

(Continued)

OTHER PUBLICATIONS

"Advisory Action", U.S. Appl. No. 15/974,255, Sep. 30, 2021, 3 pages.

(Continued)

*Primary Examiner* — Joseph M Santos Rodriguez
*Assistant Examiner* — Kaitlyn E Sebastian
(74) *Attorney, Agent, or Firm* — Colby Nipper PLLC

(57) ABSTRACT

An ultrasound imaging system computes real time physiological parameters from measurements of anatomical features in ultrasound image data using a neural network to identify the location of the anatomical features. In one embodiment, cardiac parameters are computed from endocardial wall tracings in M-mode ultrasound image data that are identified by the neural network.

27 Claims, 5 Drawing Sheets

(51) Int. Cl.
*A61B 8/06* (2006.01)
*A61B 8/14* (2006.01)

(52) U.S. Cl.
CPC .......... *A61B 8/5261* (2013.01); *A61B 8/5276* (2013.01); *A61B 8/5284* (2013.01); *A61B 8/5292* (2013.01)

(56) References Cited

U.S. PATENT DOCUMENTS

| | | | |
|---|---|---|---|
| 2005/0038340 | A1 | 2/2005 | Vaezy et al. |
| 2006/0025689 | A1 | 2/2006 | Chalana et al. |
| 2006/0074315 | A1 | 4/2006 | Liang et al. |
| 2006/0270934 | A1 | 11/2006 | Savord et al. |
| 2007/0196005 | A1 | 8/2007 | White et al. |
| 2010/0232665 | A1 | 9/2010 | Amir |
| 2011/0021915 | A1* | 1/2011 | Feng ............ A61B 5/7267 600/443 |
| 2012/0134576 | A1 | 5/2012 | Sharma et al. |
| 2013/0116578 | A1 | 5/2013 | An et al. |
| 2014/0052001 | A1 | 2/2014 | Ionasec et al. |
| 2016/0157829 | A1* | 6/2016 | Lee ............ A61B 8/488 600/441 |
| 2017/0231602 | A1 | 8/2017 | Venkataraman et al. |
| 2017/0360411 | A1 | 12/2017 | Rothberg et al. |
| 2019/0343490 | A1 | 11/2019 | White |

FOREIGN PATENT DOCUMENTS

| | | |
|---|---|---|
| JP | 2003-265479 A | 9/2003 |
| JP | 2004-208858 A | 7/2004 |
| JP | 2006-522664 A | 10/2006 |
| JP | 2008-531173 A | 8/2008 |
| WO | WO 2010/103085 A1 | 9/2010 |

OTHER PUBLICATIONS

"Extended European Search Report", EP Application No. 19800213.1, Dec. 21, 2021, 10 pages.
"Final Office Action", U.S. Appl. No. 15/974,255, May 31, 2022, 44 pages.
"Final Office Action", U.S. Appl. No. 15/974,255, Sep. 15, 2021, 50 pages.
"Final Office Action", U.S. Appl. No. 15/974,255, Oct. 27, 2020, 39 pages.
"Foreign Office Action", EP Application No. 19800213.1, Jun. 1, 2023, 5 pages.
"Non-Final Office Action", U.S. Appl. No. 15/974,255, Mar. 22, 2021, 43 pages.
"Non-Final Office Action", U.S. Appl. No. 15/974,255, Jun. 30, 2020, 25 pages.
"Non-Final Office Action", U.S. Appl. No. 15/974,255, Dec. 10, 2021, 41 pages.
"Notice of Allowance", U.S. Appl. No. 15/974,255, Sep. 15, 2022, 10 pages.
U.S. Appl. No. 15/974,255 U.S. Pat. No. 11,553,900, filed May 8, 2018 (Jan. 17, 2023).
U.S. Appl. No. 15/974,255, Dec. 23, 2022 Issue Fee Payment.
U.S. Appl. No. 15/974,255, Sep. 15, 2022 Notice of Allowance.
U.S. Appl. No. 15/974,255, Aug. 26, 2022 Notice of Appeal Filed.
U.S. Appl. No. 15/974,255, May 31, 2022 Final Office Action.
U.S. Appl. No. 15/974,255, Apr. 11, 2022 Response to Non-Final Office Action.
U.S. Appl. No. 15/974,255, Dec. 10, 2021 Non-Final Office Action.
U.S. Appl. No. 15/974,255, Oct. 11, 2021 Request for Continued Examination (RCE).
U.S. Appl. No. 15/974,255, Sep. 30, 2021 Advisory Action.
U.S. Appl. No. 15/974,255, Sep. 15, 2021 Response After Final Action.
U.S. Appl. No. 15/974,255, Jul. 15, 2021 Final Office Action.
U.S. Appl. No. 15/974,255, Jun. 22, 2021 Response to Non-Final Office Action.
U.S. Appl. No. 15/974,255, Mar. 22, 2021 Non-Final Office Action.
U.S. Appl. No. 15/974,255, Jan. 25, 2021 Amendment and Request for Continued Examination (RCE).
U.S. Appl. No. 15/974,255, Oct. 27, 2020 Final Office Action.
U.S. Appl. No. 15/974,255, Sep. 30, 2020 Response to Non-Final Office Action.
U.S. Appl. No. 15/974,255, Sep. 22, 2020 Applicant Initiated Interview Summary.
U.S. Appl. No. 15/974,255, Jun. 30, 2022 Non-Final Office Action.
International Search Report and Written Opinion mailed Aug. 16, 2019 in International Application No. PCT/US2019/030513.
Madani et al., "Fast and accurate view classification of echocardiograms using deep learning," Digital Medicine 1(6):1-8 (2018).

* cited by examiner

ULTRASOUND SYSTEM WITH AUTOMATED WALL TRACING

CROSS-REFERENCE TO RELATED APPLICATION(S)

The present application is related to, and claims the benefit of, U.S. patent application Ser. No. 15/974,255 filed May 8, 2018, which is herein incorporated by reference in its entirety.

TECHNICAL FIELD

The disclosed technology relates to ultrasound imaging systems and in particular to ultrasound systems that provide real time physiological measurements from ultrasound image data.

BACKGROUND

Due to ease of use and its non-ionizing radiation, ultrasound is becoming an increasingly used imaging modality for human and animal subjects. In addition to providing images of internal body tissues, ultrasound can also be used to provide quantitative assessments of physiological functions that can be used by researchers or medical care providers. One example of such quantitative assessments are those related to cardiac function. Physiological parameters such as ejection fraction (EF), fractional shortening (FS), stoke volume (SV) and cardiac output (CO) are well known measurements used in diagnosing and staging patients. Among the four standard functional parameters, ejection fraction (EF), which is a measure of how well the heart is pumping blood, is one key to diagnosing and staging heart failure. Each of these parameters can be calculated from measurements made from ultrasound image data.

In conventional ultrasound systems, a physician, ultrasound technician or other skilled health care provider that wants an indication of cardiac output first performs an ultrasound examination. After the ultrasound image data are captured and stored, the operator reviews the image data and manually places markers on the images over certain tissue features or sends the images to a radiologist to place the markers. The distance between these markers is then used to compute the physiological parameters. Having the ability to display such physiological parameters in real time while a subject is being examined will enable a medical provider to make diagnostic decisions more rapidly without stopping to make measurements manually or having to send images to a radiology department.

SUMMARY

To address the problems discussed above and others, the disclosed technology relates to an ultrasound imaging system that computes real time physiological parameters from measurement of features in ultrasound image data using a neural network. In one embodiment, a processor of the ultrasound imaging system produces ultrasound images that are provided to a trained neural network that identifies a physical feature. Once the physical features are identified, the processor determines measurements of the features and computes one or more physiological parameters.

Cardiac functional parameters can be calculated using M-Mode images acquired from the parasternal long axis view. A typical method involves making measurements of the thickness of the interventricular septum (IVS) or the right ventricle wall (RVID), the left ventricular interior diameter (LVID), the left ventricle posterior wall (LVPW) at both systole (;s) and diastole (;d), and the heart rate. In some cases, only the LVID measurements at both systole and diastole are needed to calculate measures of cardiac function. These measurements can be made manually on a static (during review; not live) image, and can include measurements of the heart rate (either directly from the image or by using the ECG signal if available).

The same anatomical measurements and functional calculations may also be achieved using a trace of the anterior and posterior heart wall boundary (endocardial border). In this case, LVID;d and LVID;s are measured at the minimum and maximum separation points between these two traces. The heart rate can be extracted using the time difference from multiple systole-to-systole periods or from the ECG trace if available.

In one disclosed embodiment, the processor in the ultrasound system computes cardiac output parameters in real time as ultrasound images are captured. A processor provides M-Mode ultrasound images to a neural network that is trained to identify the endocardial border from the images. From the identified location of the walls of the endocardium, the processor can compute cardiac parameters that are displayed in real time along with ultrasound image data. This process can be applied to clinical (human) imaging situations as well as preclinical (animal models such as mouse and rat) imaging.

In the disclosed embodiment, automatic endocardial wall tracing relieves the operator from the laborious work of manual tracing and also provides multiple systolic and diastolic points that can be measured to provide cycle averaging. It also facilitates the option of real time measurements, which would be impossible otherwise.

DETAILED DESCRIPTION

Figure 1:
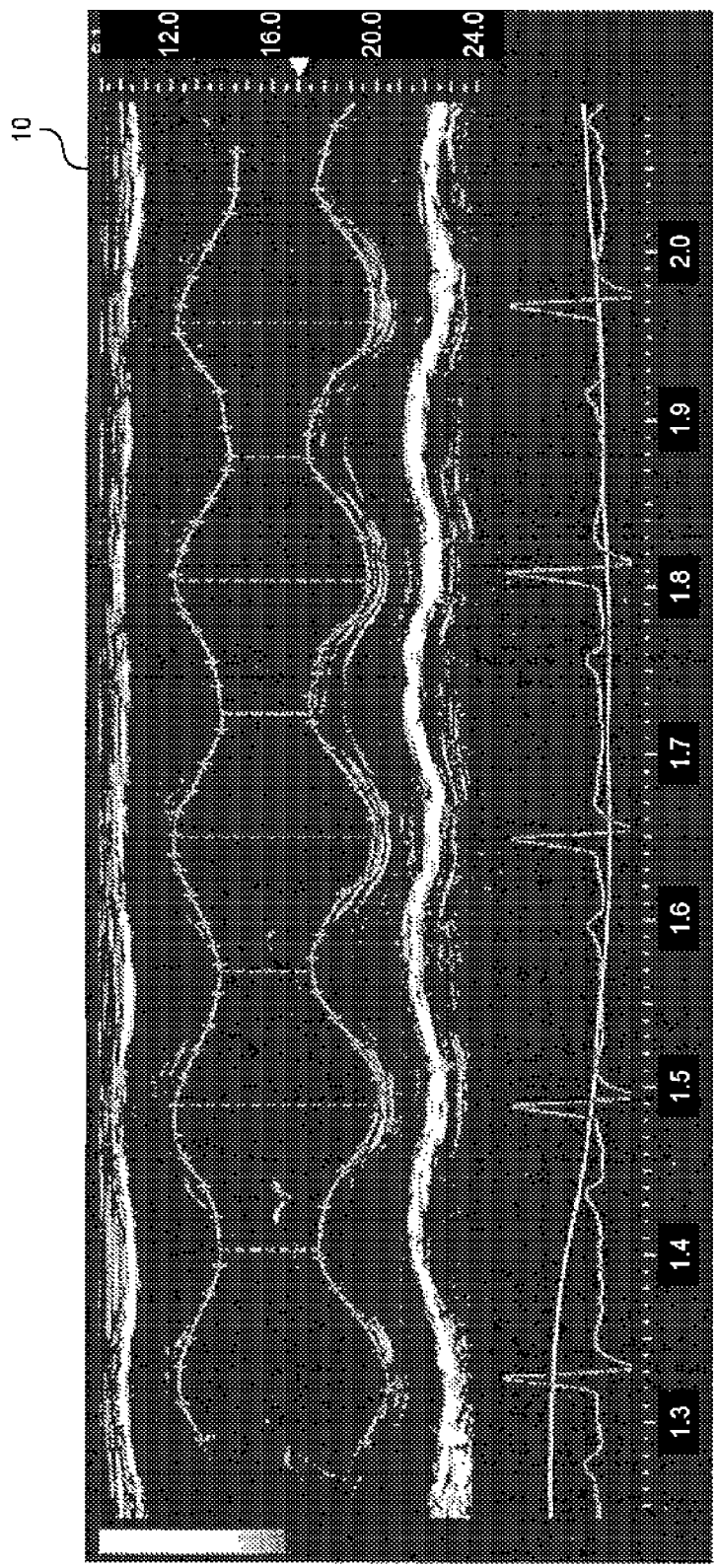
FIG. 1 shows an example of a pair of manually made endocardial traces (LV) on an M-Mode ultrasound image.

As described above, the conventional method of computing physiological parameters from ultrasound image data is to manually place one or more markers on an ultrasound image and compute the parameters from the measurements associated with the placement of the markers. FIG. 1 shows an example of an M-Mode ultrasound image 10 of a mouse cardiac left ventricle that is beating over a number of cardiac cycles. The image includes a number of markers (e.g. plus "+" signs) that are manually placed by a user over the contour of physical features that can be seen in the image data. In this example, the markers are located on a pair of opposing endocardial walls that compress toward each other during the systole phase of the cardiac cycle and expand away from each other during diastole phase of the cardiac cycle. A processor in the ultrasound system computes a pair of curves that join the manually placed markers using a curve fitting technique such as splines or the like. The distance between the upper curve and the lower curve at the systolic and diastolic points in the cardiac cycle allows various cardiac parameters to be computed. The ultrasound image 10 also includes EKG and respiratory information obtained from other sensors connected to the ultrasound machine.

While the approach shown in FIG. 1 allows the accurate computation of the physiological parameters, it requires that the user manually place the markers on a previously obtained image. If the physical features are readily identified, the marking can be accomplished in about 30 seconds. However, the process can take longer if the physical feature is not easy to see in the image. As will be described in detail below, the disclosed technology relates to an ultrasound system that uses software or programmable logic to automatically identify physical features in an image. This allows physiological parameters to be computed and shown to the operator in real time.

Figure 2:
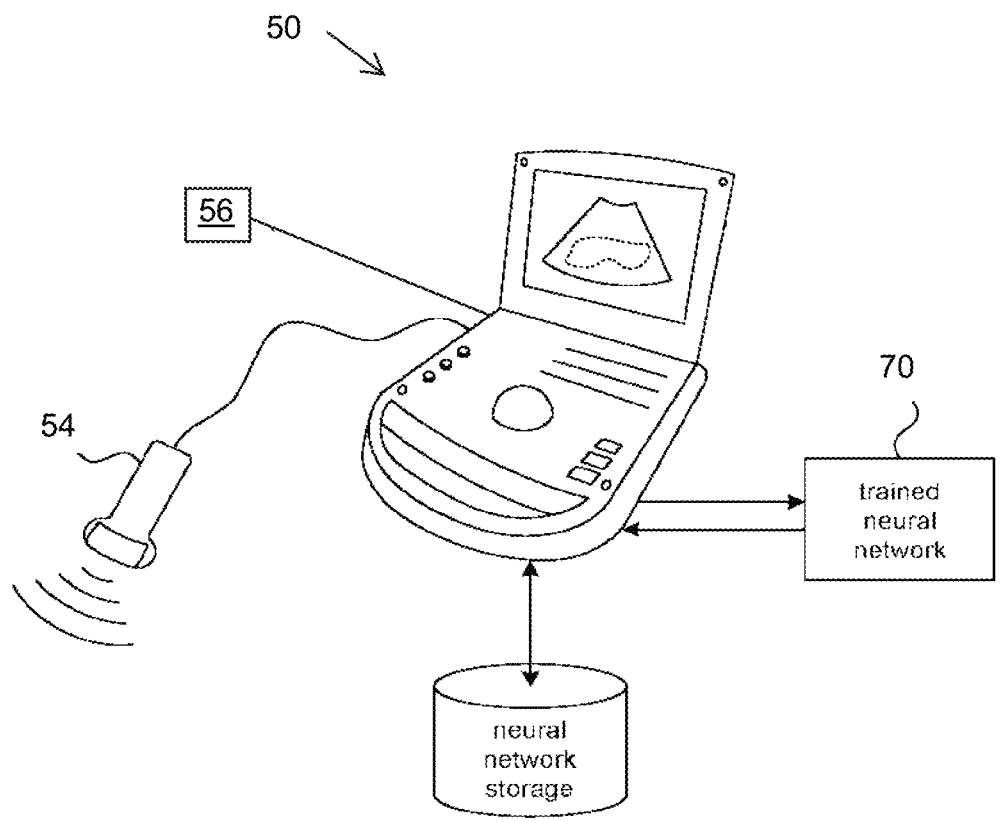
FIG. 2 shows a representative ultrasound system for making real time physiological measurements from ultrasound image data in accordance with an embodiment of the disclosed technology.

FIG. 2 shows a representative ultrasound system with which the disclosed technology can be implemented. An ultrasound imaging system 50 can comprise a hand held, portable or cart-based imaging system. The ultrasound system 50 connects with one or more ultrasound transducers 54 that transmit ultrasound signals into a subject (not shown) and receive the corresponding echo signals from the subject. In some embodiments, the ultrasound system 50 can receive signals from one or more additional external sensors 56 such as pulse oximeter (SpO2) sensors, electrocardiogram (EKG) sensors, respiration sensors or the like. The ultrasound imaging system 50 includes one or more displays on which ultrasound data are displayed. The displays may include a touch sensitive display such that the operator can operate the system using touch commands. In some embodiments, additional controls (track balls, buttons, keys, trackpad, voice activated controls etc.) may also be provided with which to interact with the operator. The ultrasound imaging system 50 also includes communication circuitry to connect to one or more remotely located systems through a wired or wireless computer communication link.

The ultrasound imaging system 50 includes image processing circuitry having one or more processors (e.g. central processing units (CPUs), digital signal processors (DSPs), graphic processing units (GPUs), application-specific integrated circuits (ASICs), field programmable gate arrays (FPGAs) or a combination thereof) that are configured to execute programmed instructions stored in a processor readable memory or that perform pre-determined logical operations to implement a neural network that is trained to analyze ultrasound image data in order to mark the location of physical features in the image. In the disclosed embodiment, the physical features are a pair of opposing ventricle walls (anterior left ventricular wall/interventricular septum and the posterior left ventricular wall) that define the volume of the left ventricle. In this embodiment, the ultrasound image is an M-Mode ultrasound image obtained in a parasternal long axis view (PLAX). Although the disclosed embodiment is described with respect to identifying the location of the opposing ventricular walls, it will be appreciated that the disclosed technology is extendable to identifying other tissue structures in ultrasound image data including vessel walls, heart valves, esophageal tissue in the case of transesophageal imaging or stomach or intestine tissue in the case of gastric imaging.

The processor in the ultrasound imaging system is configured to provide ultrasound image data to a neural network 70 that is trained to identify the location of the desired physical features. In the disclosed embodiment, the neural network 70 is trained to identify the upper and lower boundaries of the endocardial walls and the interior of the cardiac ventricle in a column of ultrasound image pixel data. In an ultrasound image, the boundary is generally characterized by a relatively bright reflection that is adjacent a black region representing a volume filled with non-reflecting blood. However, when used with high frequency imaging (e.g. 20+ MHz), ultrasound is reflected from the blood cells in the ventricle making the boundary area more difficult to visually detect.

Figure 3:
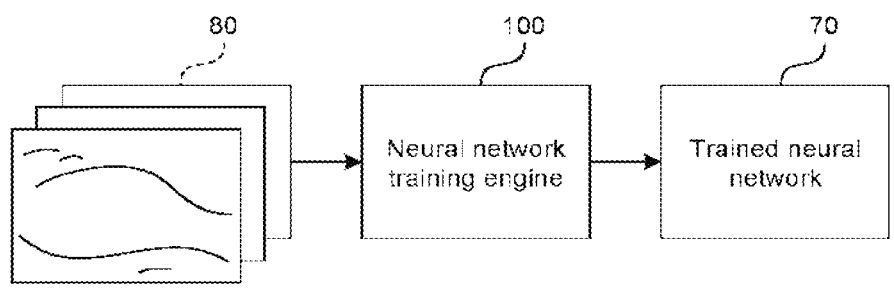
FIG. 3 shows how a neural network is trained with a number of test images in accordance with an embodiment of the disclosed technology.

To train the neural network 70, a number of test images 80 are provided to a neural network training engine 100 as shown in FIG. 3. The test images 80 are images of ultrasound data with the features to be identified (e.g. the vessel walls) previously expertly marked. In one embodiment, the images are a uniform size such as 256 pixels wide by 128 pixels high with each pixel having an eight-bit black and white brightness value. Other image sizes can also be used such as 256 pixels wide by 256 pixels high or 512 pixels wide by 64 pixels high. In this data representation, each column of data is an acquired line of ultrasound data. Data is acquired at the pulse repetition frequency (PRF). For example, if the PRF is 1000 Hz and the image consists of 256 lines or columns of data then the data set comprises of a time window of 256 ms. For small animal imaging, this encompasses a number of cardiac cycles. For clinical imaging either the number of data lines used must be increased or the PRF reduced to contain more than one cycle of data. The pixels in each column represent samples at different depths in the image. The first pixel in each column is at the shallowest depth. In one embodiment the image data are obtained from M-Mode scans at a pulse repetition frequency (PRF) of 1500 Hz. Other PRF values could also be used; for example 1000, 1250, 1750, 2000 Hz or higher.

As will be appreciated by those skilled in the art of machine learning, a large number (e.g. 1,000-14,000 or more) training images are supplied to the neural network training engine 100 to allow the engine to determine a number of filter weights and bias values so that a convolutional neural network using the weights and bias value will return the most likely pixel locations in a column of image data that represent the ventricle walls. To one skilled in the art, it is also understandable that the total number of training images can be increased using data augmentation whereby the initial base set of images are increased though linear and nonlinear modifications thereby producing additional training data. For example, augmentation may include both linear and nonlinear scaling or brightness or contrast changes.

In one embodiment, the neural network 70 is configured to receive an input image of the same size with which the neural network was trained (e.g. 256×128×1) and to produce an output data set (256×2) marking the two most likely locations of the ventricle wall boundaries in each column of image pixel data. Other input image sizes such as 512×

128×1 or 256×256×1 with corresponding output sizes of 512×2 or 256×2 can also be used.

In one embodiment, the training data images were collected and approximately 750 traces were manually labeled, meaning the anterior and posterior left ventricular chamber walls were traced. Increasing the number of labeled training data increases the likelihood of an accurate generalization of the problem during training of the neural network. These data were formatted using C++ and Python. Data augmentation was performed to increase the amount of training data available. With augmentation, approximately 20 to 1 increase in semi-unique data instances were obtained from the initial labeled data sets.

A model framework setup using Keras, Tensorflow, and Python was used. A number of different machine learning models were tested. For one skilled it the art, it can be understood that a number of different machine learning models can be employed. For example, variants of freely available models can be used such as VGG5, VGG16 (Visual Geometry Group at Oxford), and Mobile Net (Google). Custom models can also be developed. Tradeoffs using different models can include prediction accuracy and size which will affect inference speed on embedded devices. These models were modified such that they conformed to the input size and output requirements of this specific problem.

For each of these models, the input data sets consisted of 256 lines of M-Mode data at a measured PRF of 1500 Hz. Other PRFs can also be used such as but not limited to 1000, 1250, 1750 or 2000 Hz. The data were resampled to 128 depth samples. Other depths could also be used such as 64 samples, or 256 samples. The number of samples also need not be a power of 2. Data were 8-bit single channel. For mouse data, the data length corresponds to approximately 1-2 heart cycles depending on the heart rate. As will be appreciated, for other applications such as for human acquired data sets, the heart rate is much lower. The data might be scaled appropriately to fit the same 1-2 heart cycles; or a different input size data set may be used or a different PRF setting may be used. Changing either PRF or input size will change the amount of time represented in the image.

In the embodiment described, the ultrasound image is comprised of pixel data that is in a format that is ready to be displayed on a video monitor. It will be appreciated that the disclosed technology could also be used with other types of image data such as pre-scan conversion image data or raw ultrasound data. Therefore, as used herein, the term image data is to refer to ultrasound data that is representative of an area of interest and not only to scan converted ultrasound data.

Figure 4:
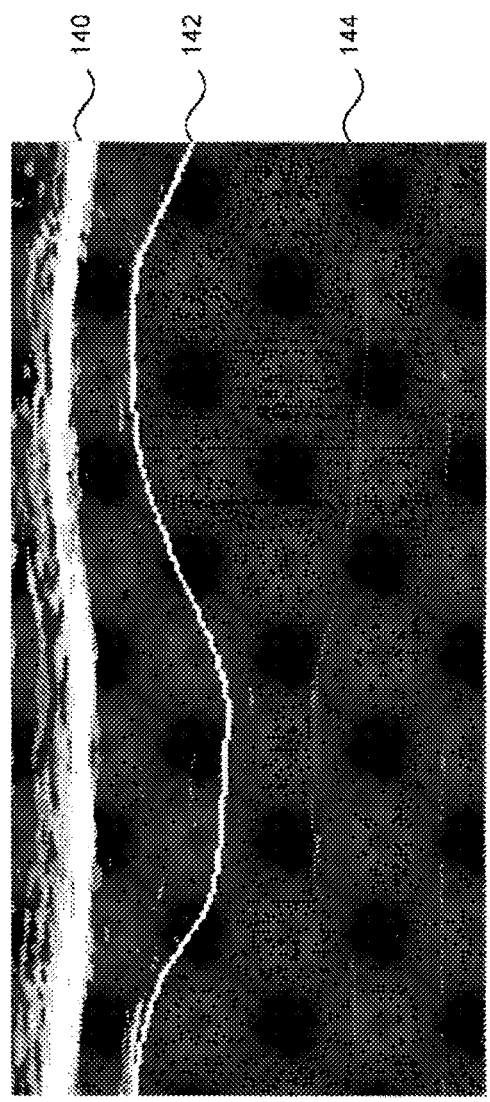
FIG. 4 shows a portion of an M-Mode ultrasound image that is input to a trained neural network and output data from the neural network indicating the location of the endocardium in the image in accordance with an embodiment of the disclosed technology.

The output data format is 2 data points (position of anterior and posterior wall boundary) for each of the 256 input lines (see FIG. 4). (Output data size 256×2). Further experimentation could include expanding the data length to include more lines.

Neural network models themselves are generally interchangeable, with some providing advantages over others. For example, computational complexity and output accuracy are considerations. Currently excellent results are found using a variation of Mobile Net V1 (Google) model. Shown below is an example of this model showing the different layers and modifications required to conform to the input image size (256×128). Modifications could include using a different model, changing the number of layers, or adding additional layers such as dense layers or addition convolutional layers.

| Modified Mobile Net V1 model. | | |
| --- | --- | --- |
| Layer (type) | Output Shape | Param # |
| vsi_input_layer (InputLayer) | (None, 256, 128, 1) | 0 |
| conv1 (Conv2D) | (None, 128, 64, 32) | 288 |
| convi_bn (BatchNorm) convi_relu (Activation) | (None, 128, 64, 32) | 128 |
| conv_dw_1 (DepthwiseConv2D) | (None, 128, 64, 32) | 0 |
| conv_dw_1 | (None, 128, 64, 32) | 288 |
| conv_dw_1_bn (BatchNorm) | (None, 128, 64, 32) | 128 |
| conv_dw_1_relu (Activation) | (None, 128, 64, 32) | 0 |
| conv_pw_1 (Conv2D) | (None, 128, 64, 64) | 2048 |
| conv_pw_1_bn (BatchNorm) | (None, 128, 64, 64) | 256 |
| conv_pw_1_relu (Activation) | (None, 128, 64, 64) | 0 |
| conv_dw_2 (DepthwiseConv2D) | (None, 64, 32, 64) | 576 |
| conv_dw_2_bn (BatchNorm) | (None, 64, 32, 64) | 256 |
| conv_dw_2_relu (Activation) | (None, 64, 32, 64) | 0 |
| conv_pw_2 (Conv2D) | (None, 64, 32, 128) | 8192 |
| conv_pw_2_bn (BatchNorm) | (None, 64, 32, 128) | 512 |
| conv_pw_2_relu (Activation) | (None, 64, 32, 128) | 0 |
| conv_dw_3 (DepthwiseConv2D) | (None, 64, 32, 128) | 1152 |
| conv_dw_3_bn (BatchNorm) | (None, 64, 32, 128) | 512 |
| conv_dw_3_relu (Activation) | (None, 64, 32, 128) | 0 |
| conv_pw_3 (Conv2D) | (None, 64, 32, 128) | 16384 |
| conv_pw_3_bn (BatchNorm) | (None, 64, 32, 128) | 512 |
| conv_pw_3_relu (Activation) | (None, 64, 32, 128) | 0 |
| conv_dw_4 (DepthwiseConv2D) | (None, 32, 16, 128) | 1152 |
| conv_dw_4_bn (BatchNorm) | (None, 32, 16, 128) | 512 |
| conv_dw_4_relu (Activation) | (None, 32, 16, 128) | 0 |
| conv_pw_4 (Conv2D) | (None, 32, 16, 256) | 32768 |
| conv_pw_4_bn (BatchNorm) | (None, 32, 16, 256) | 1024 |
| conv_pw_4_relu (Activation) | (None, 32, 16, 256) | 0 |
| conv_dw_5 (DepthwiseConv2D) | (None, 32, 16, 256) | 2304 |
| conv_dw_5_bn (BatchNorm) | (None, 32, 16, 256) | 1024 |
| conv_dw_5_relu (Activation) | (None, 32, 16, 256) | 0 |
| conv_pw_5 (Conv2D) | (None, 32, 16, 256) | 65536 |
| conv_pw_5_bn (BatchNorm) | (None, 32, 16, 256) | 1024 |
| conv_pw_5_relu (Activation) | (None, 32, 16, 256) | 0 |
| conv_dw_6 (DepthwiseConv2D) | (None, 16, 8, 256) | 2304 |
| conv_dw_6_bn (BatchNorm) | (None, 16, 8, 256) | 1024 |
| conv_dw_6_relu (Activation) | (None, 16, 8, 256) | 0 |
| conv_pw_6 (Conv2D) | (None, 16, 8, 512) | 131072 |
| conv_pw_6_bn (BatchNorm) | (None, 16, 8, 512) | 2048 |
| conv_pw_6_relu (Activation) | (None, 16, 8, 512) | 0 |
| conv_dw_7 (DepthwiseConv2D) | (None, 16, 8, 512) | 4608 |
| conv_dw_7_bn (BatchNorm) | (None, 16, 8, 512) | 2048 |
| conv_dw_7_relu (Activation) | (None, 16, 8, 512) | 0 |
| conv_pw_7 (Conv2D) | (None, 16, 8, 512) | 262144 |
| conv_pw_7_bn (BatchNorm) | (None, 16, 8, 512) | 2048 |
| conv_pw_7_relu (Activation) | (None, 16, 8, 512) | 0 |
| conv_dw_8 (DepthwiseConv2D) | (None, 16, 8, 512) | 4608 |
| conv_dw_8_bn (BatchNorm) | (None, 16, 8, 512) | 2048 |
| conv_dw_8_relu (Activation) | (None, 16, 8, 512) | 0 |
| conv_pw_8 (Conv2D) | (None, 16, 8, 512) | 262144 |
| conv_pw_8_bn (BatchNorm) | (None, 16, 8, 512) | 2048 |
| conv_pw_8_relu (Activation) | (None, 16, 8, 512) | 0 |
| conv_dw_9 (DepthwiseConv2D) | (None, 16, 8, 512) | 4608 |
| conv_dw_9_bn (BatchNorm) | (None, 16, 8, 512) | 2048 |
| conv_dw_9_relu (Activation) | (None, 16, 8, 512) | 0 |
| conv_pw_9 (Conv2D) | (None, 16, 8, 512) | 262144 |
| conv_pw_9_bn (BatchNorm) | (None, 16, 8, 512) | 2048 |
| conv_pw_9_relu (Activation) | (None, 16, 8, 512) | 0 |
| conv_dw_10 (DepthwiseConv2D) | (None, 16, 8, 512) | 4608 |
| conv_dw_10_bn (BatchNorm) | (None, 16, 8, 512) | 2048 |
| conv_dw_10_relu (Activation) | (None, 16, 8, 512) | 0 |
| conv_pw_10 (Conv2D) | (None, 16, 8, 512) | 262144 |
| conv_pw_10_bn (BatchNorm) | (None, 16, 8, 512) | 2048 |
| conv_pw_10_relu (Activation) | (None, 16, 8, 512) | 0 |
| conv_dw_11 (DepthwiseConv2D) | (None, 16, 8, 512) | 4608 |
| conv_dw_11_bn (BatchNorm) | (None, 16, 8, 512) | 2048 |
| conv_dw_11_relu (Activation) | (None, 16, 8, 512) | 0 |
| conv_pw_11 (Conv2D) | (None, 16, 8, 512) | 262144 |
| conv_pw_11_bn (BatchNorm) | (None, 16, 8, 512) | 2048 |
| conv_pw_11_relu (Activation) | (None, 16, 8, 512) | 0 |
| conv_dw_12 (DepthwiseConv2D) | (None, 8, 4, 512) | 4608 |
| conv_dw_12_bn (BatchNorm) | (None, 8, 4, 512) | 2048 |
| conv_dw_12_relu (Activation) | (None, 8, 4, 512) | 0 |
| conv_pw_12 (Conv2D) | (None, 8, 4, 1024) | 524288 |
| conv_pw_12_bn (BatchNorm) | (None, 8, 4, 1024) | 4096 |
| conv_pw_12_relu (Activation) | (None, 8, 4, 1024) | 0 |
| conv_dw_13 (DepthwiseConv2D) | (None, 8, 4, 1024) | 9216 |

-continued

Modified Mobile Net V1 model.

| Layer (type) | Output Shape | Param # |
|---|---|---|
| conv_dw_13_bn (BatchNorm) | (None, 8, 4, 1024) | 4096 |
| conv_dw_13_relu (Activation) | (None, 8, 4, 1024) | 0 |
| conv_pw_13 (Conv2D) | (None, 8, 4, 1024) | 1048576 |
| conv_pw_13_bn (BatchNorm) | (None, 8, 4, 1024) | 4096 |
| conv_pw_13_relu (Activation) | (None, 8, 4, 1024) | 0 |
| block6_conv1 (Conv2D) | (None, 8, 4, 512) | 4718592 |
| batch_normalization_1 (BatchNorm) | (None, 8, 4, 512) | 2048 |
| leaky_re_lu_1 (LeakyReLU) | (None, 8, 4, 512) | 0 |
| block6_pool (MaxPooling2D) | (None, 4, 2, 512) | 0 |
| block7_conv1 (Conv2D) | (None, 4, 2, 256) | 1179648 |
| batch_normalization_2 (BatchNorm) | (None, 4, 2, 256) | 1024 |
| leaky_re_lu_2 (LeakyReLU) | (None, 4, 2, 256) | 0 |
| block7_pool (MaxPooling2D) | (None, 2, 1, 256) | 0 |
| vsi_output_layer (Flatten) | (None, 512) | 0 |

Total parameters: 9,129,600
Trainable parameters: 9,106,176
Non-trainable parameters: 23,424

The model shown above is successful because it generates accurate results and is relatively small enabling fast computation (e.g. about 300 ms. per 256 line image on a CPU). A Python framework using Keras and Tensorflow was used to train this model using the prepared and augmented data. An Adam optimizer with variable learning rate was employed over approximately 1 million training examples. Other optimizers can be used; for example SGD (Stochastic Gradient Descent). The tradeoffs using different optimizers include convergence time, and training speed. A combination of 2 or more different optimizers can also be used. Using an Amazon Web Services (AWS) server and a K80 Nvidia GPU, the time to train the neural network 70 was approximately 12 hours.

Using an isolated set of approximately 10% of the original data set, the accuracy of the model was evaluated. For the test cases, it was demonstrated that the median accuracy of endocardial wall identification was 96%.

As indicated above, once the neural network 70 has been trained, the network is ready for use in the ultrasound imaging system 50 to identify physical features in ultrasound image data in real time. In some embodiments, the processor of the ultrasound system 50 is programmed to execute the trained neural network 70 and to supply the neural network with image data obtained from the subject. The neural network returns the likely locations of the physical features it is trained to identify. FIG. 4 shows a representative M-Mode ultrasound image 140 containing an upper trace 142 representing an anterior wall and a lower trace 144 representing a posterior wall of a heart muscle that have been identified by the neural network 70.

With the traces 142, 144 provided by the trained neural network, the processor analyzes the traces to determine the distance where the traces are 1) closest together and 2) farthest apart. These distances represent the heart muscle at the systolic and diastolic phases of the cardiac cycle. In one embodiment, the location can be determined by analyzing the distance (in pixels) in each column of the image (e.g. by searching the image columns for the minimum and maximum pixel gap). In another embodiment, the systole and diastole of the cardiac cycle can be determined from an EKG signal that is obtained simultaneously with the ultrasound data. Knowing the time difference represented between each pixel in a column, the speed of ultrasound in the tissue and the number of samples in a column between the identified locations on the traces 142, 144, the physical distance between the heart walls in the subject is calculated by the processor.

With the distances calculated, the physiological parameters from the traces are computed by the processor. In one embodiment, knowing the distance between the cardiac walls at the various points in the cardiac cycle, the cardiac parameters can be calculated according to the equations and the normal expected ranges:

ejection fraction EF=$(lvedv-lvesv)/lvedv \times 100$.
(Male=52-72%)(Female=54-74%)$ASE$ fractional shortening FS=$(lvedd-lvesd)/lvedd \times 100$.
(Male 27-45%) (Female=25-43%)

stroke volume SV=$lvedv-lvesv$ cardiac output CO=Stroke Volume×HR, Normal Range=(4.0-8.0 L/min) as understood by those skilled in the art Ventricular volumes calculated from ventricular wall measurements can be subject to interpretation and may vary. In one embodiment, they are approximated by the following equations. These are exemplary and may be adjusted depending on the type of subject being examined or other factors.

*lvedv* is the left ventricular end-diastolic volume, which in one embodiment=$(7/(2.4+lvedd))*lvedd^3$

*lvesv* is the left ventricular end-systolic volume, which in one embodiment=$(7/(2.4+lvesd))*lvesd^3$ lvedd is the left ventricular end-diastolic dimension (mm)
lvesd is the left ventricular end-systolic dimension (mm)

Figure 6:
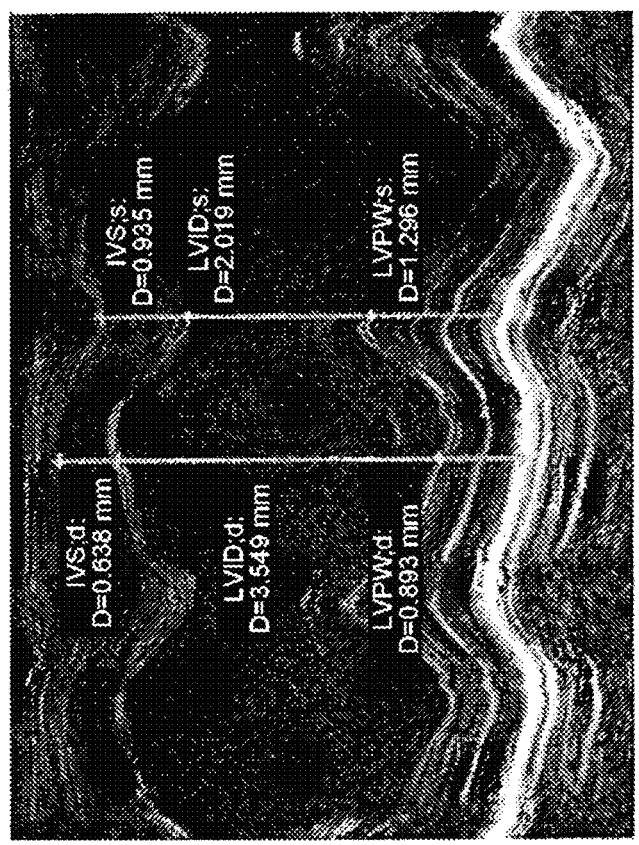
FIG. 6 shows representative M-Mode thickness measurements of the anterior wall, chamber, and posterior wall.

As shown in FIG. 6, the processor executes instructions to calculate and display measurements on the detected physical features such as the distance between physical features, the angle between physical features, the area of the features etc. In the example shown in FIG. 6, the distances in millimeters between the anterior and posterior ventricular walls at systole and diastole are calculated and displayed.

In some embodiments, the processor can also execute instructions to calculate the distances between the outer 2 walls for additional left ventricular assessment. For example, the LV Mass can be calculated when the distances between all 4 walls have been measured. In this example; the processor computes the distances between all 4 cardiac walls at the same time.

In some embodiments, the ultrasound system 50 is connected to a respiratory monitor that indicates to the ultrasound system whether the subject is breathing during the acquisition of ultrasound images. Image data obtained during breathing can include motion artifacts that make the physiological parameters less reliable. Therefore, in some embodiments, the processor is programmed to ignore ultrasound imaging data that are obtained during a breath. This is particularly true in animal studies where breathing introduces large motion artifacts. For human subjects, the subject is generally asked to hold their breath during image capture.

In some embodiments the operator can select a start and stop point on the M-Mode data were representing a region over which the walls are to be traced and physiological parameters are calculated. In other embodiments, the respiration signal can be used to automatically determine suitable start and stop points. In this case, the physiological parameters can be calculated automatically without any user intervention. They can also be calculated in real time. Other methods can also be used to determine the selection of suitable start and stop points such as looking at the variance of the detected output points.

Figure 5:
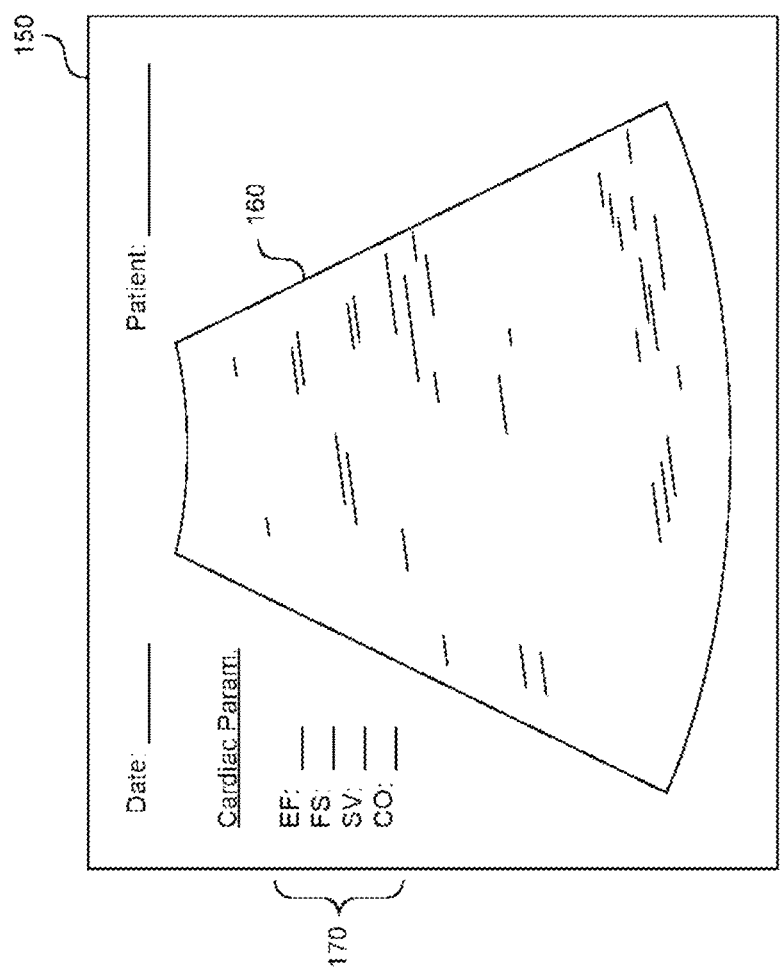
FIG. 5 illustrates an exemplary user interface of an ultrasound imaging system showing image data and one or more physiological parameters that are computed in real time from physical features identified by the neural network in accordance with an embodiment of the disclosed technology.

Once the physiological parameters are computed, one or more of the parameters are displayed on a user interface screen as shown in FIG. 5. In this embodiment, the display 150 may include an image 160 of the tissue being examined. Such an image 160 may be the same image used to compute the physiological parameters. For example, if M-Mode image data are provided to the trained neural network to compute the physiological parameters, the M-Mode image may be displayed on the display 150. In some embodiments, the image 160 may be a different imaging modality (B-Mode, Doppler, Power Doppler etc.) than the modality used to obtain the ultrasound images provided to the neural network. In this embodiment, the ultrasound system interleaves imaging modalities to produce B-Mode images that are displayed to the user and M-Mode ultrasound images for the neural network in the background and that are not shown to the user.

The display 150 includes one or more of the physiological parameters 170 that are computed with the physical features identified by the neural network. As will be appreciated from the discussion above, the physiological parameters are computed in real time from ultrasound image data produced by the imaging system. Because the physical features are identified by the neural network in real time, the operator of the ultrasound system does not have to manually mark previously obtained images or send them to a radiologist. The result is that the operator can use the physiological parameter information to make quicker decisions regarding the subject's physical condition.

In some embodiments, the processor is programmed to calculate the physiological parameters over a number of cardiac cycles. Signals from an EKG or other pulse sensor can be read by the processor to determine a number of cardiac cycles and ultrasound image frames can be supplied to the trained neural network to identify the tissue features and calculate the physiological parameters from the identified tissue features. Calculated values from the different cardiac cycles can be averaged and displayed to the operator. In other embodiments, other statistical measurements such as the variance, maximum or minimum of the calculated values can be determined and displayed.

In some instances, the processor is programmed to produce an alert (visual, audible, tactile etc.) if the variance of the computed physiological parameters exceeds a baseline value by more than a threshold value (for example but not limited to +1-2%, +/−5%, +/−10% or greater from the baseline value). Such an alert may indicate a patient condition or a problem with detecting the echo data (e.g. probe misalignment or malfunction etc.) The baseline and/or threshold values can be based on determined normal ranges for the subject (species, age, race, sex, weight, previously medical history, medications taken etc.) or previous or current measurements from the same subject. Such information can be entered by the operator of the ultrasound imaging machine or can be read by the processor from an electronic patient or subject record (radio frequency (RF) id tag on an animal cage, information encoded on a patient's wrist, bar code, quick response (OR) code, etc.). In some embodiments, current physiological parameters are compared with or displayed alongside with previous parameters that are stored in an electronic medical record.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., electrically erasable programmable read-only memory (EEPROM), flash memory, compact disc read-only memory (CD-ROM), magnetic disks, or other storage devices). The operations described in this specification can be implemented as operations performed by a data processing apparatus on instructions stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit).

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one processor or on multiple processors within the ultrasound imaging system.

Processors suitable for the execution of a computer program include, by way of example, both general and special purpose microprocessors. Generally, a processor will receive instructions and data from a read-only memory or a random access memory or both. Devices suitable for storing computer program instructions and data include all forms of non-volatile memory, media and memory devices, including by way of example semiconductor memory devices, e.g., erasable programmable read-only memory (EPROM), EEPROM, and flash memory devices; magnetic disks, e.g., internal hard disks or removable disks; magneto-optical disks; and CD-ROM and digital versatile disk-read only memory (DVD-ROM) disks. The processor and the memory can be supplemented by, or incorporated in, special purpose logic circuitry.

To provide for interaction with a user, embodiments of the subject matter described in this specification can be implemented on an ultrasound imaging system having a display device, e.g., an LCD (liquid crystal display), LED (light emitting diode), or OLED (organic light emitting diode) monitor, for displaying information to the user and a keyboard and a pointing device, e.g., a mouse or a trackball, by which the user can provide input to the system. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

From the foregoing, it will be appreciated that specific embodiments of the invention have been described herein for purposes of illustration, but that various modifications may be made without deviating from the scope of the invention. Accordingly, the invention is not limited except as by the appended claims.

I claim:

1. An ultrasound imaging system, comprising:
   a transducer configured to transmit ultrasound signals generated according to a first imaging modality and a second imaging modality which is different from the first imaging modality, to a subject and to receive ultrasound echo signals corresponding to the first imaging modality and the second imaging modality from the subject, the first imaging modality and the second imaging modality being interleaved;
   a processor configured to:
     produce an ultrasound image from the ultrasound echo signals of the first imaging modality;
     produce ultrasound image data from the ultrasound echo signals of the second imaging modality; and
     identify, based on the ultrasound image data, an endocardial border in the ultrasound image; and
   a display configured to simultaneously display one or more physiological parameters and the ultrasound image;
   wherein the ultrasound image data from the echo signals of the second imaging modality is not shown on the display.

2. The ultrasound imaging system of claim 1, wherein the processor is further configured to supply the ultrasound image data to a trained neural network as a frame of the ultrasound image is created and the display is configured to simultaneously display the ultrasound image and the one or more physiological parameters.

3. The ultrasound imaging system of claim 1, wherein the display is further configured to simultaneously display the one or more physiological parameters and the ultrasound image in which the endocardial border is identified by a neural network.

4. The ultrasound system of claim 1, wherein the processor is further configured to receive signals from a respiration sensor and ignore a portion of the ultrasound image data if the portion of the image data is obtained when the respiration sensor indicates that the subject is breathing.

5. The ultrasound imaging system of claim 1, wherein the first imaging modality is a B-Mode and the second imaging modality is an M-Mode.

6. The ultrasound imaging system of claim 5, wherein the one or more physiological parameters include one or more of ejection fraction, fractional shortening, stroke volume and cardiac output.

7. The ultrasound imaging system of claim 1, wherein the processor is further configured to compute the one or more physiological parameters over a number of cardiac cycles.

8. The ultrasound imaging system of claim 7, wherein:
   the processor is further configured to determine an average of at least one physiological parameter of the one or more physiological parameters over the number of cardiac cycles; and
   the display is further configured to display the average of the at least one physiological parameter.

9. The ultrasound imaging system of claim 7, wherein:
   the processor is further configured to determine a variance of the one or more physiological parameters; and
   the display is further configured to display the variance of the one or more physiological parameters.

10. The ultrasound imaging system of claim 1, wherein the processor is further configured to:
    compare the one or more physiological parameters to a threshold and produce a comparison; and
    trigger an alert based on the comparison.

11. The ultrasound imaging system of claim 10, wherein the processor is further configured to read the threshold from a patient record.

12. The ultrasound imaging system of claim 1, wherein the processor is further configured to:
    determine additional physiological parameters from a patient record; and
    compare the one or more physiological parameters to the additional physiological parameters.

13. The ultrasound imaging system of claim 1, wherein:
    the processor is further configured to determine at least one anatomical measurement of the endocardial border; and
    the display is configured to display the at least one anatomical measurement.

14. The ultrasound system of claim 1, wherein the processor is further configured to determine when a patient's heart is in at least one of a systolic phase and a diastolic phase.

15. The ultrasound system of claim 1, wherein the processor is further configured to supply the ultrasound image data to a trained neural network that is configured to identify a physical feature, wherein training the trained neural network comprises:
    supplying a plurality of ultrasound test images having identifying features;
    acquiring data from the ultrasound test image; and
    determining a plurality of filter weights and bias values.

16. The ultrasound imaging system of claim 1, wherein a trained neural network is configured to receive an image having a number of pixel data columns that is equal to that of a plurality of images with which the neural network was trained, and to produce an output data set marking two most likely locations of the endocardial border in each image pixel data column.

17. The ultrasound imaging system of claim 1, wherein the processor is further configured to identify a first interior wall and a second interior wall of a heart muscle; and
    determine a distance between the first interior wall and the second interior wall of the heart muscle by analyzing a distance between pixels in each column of an image.

18. The ultrasound imaging system of claim 8, wherein the processor is further configured to determine the average based at least on a pulse sensor.

19. A method of operating a processor in an ultrasound imaging system, the method comprising:

producing an ultrasound image from ultrasound image data received ultrasound echo signals of a first imaging modality;

producing ultrasound image data from received ultrasound echo signals of a second imaging modality which is different from the first imaging modality: wherein the received ultrasound echo signals of the first imaging modality and the received ultrasound echo signals of the second imaging modality are interleaved;

identifying an endocardial border in the ultrasound image data; and computing one or more physiological parameters of a subject based on the endocardial border;

producing an alert if at least one of the one or more physiological parameters varies by more than a threshold amount from a baseline value; and displaying the one or more physiological parameters and the ultrasound image simultaneously;

wherein the ultrasound image data from the echo signals of the second imaging modality is not shown on the display.

20. The method of claim 19, further comprising:

determining one or more of the threshold amount and the baseline value based on a previous physiological parameter computed for the subject.

21. The method of claim 20, further comprising:

determining at least one of the baseline value and the threshold amount based on at least one of the subject's race, age, sex and previous medical history.

22. The method of claim 19, further comprising receiving signals from a respiration sensor ignoring a portion of the ultrasound image data if the portion of the image data are obtained when the respiration sensor indicates that the subject is breathing.

23. The ultrasound imaging system of claim 4, wherein the processor is further configured to automatically determine start and stop points in the ultrasound image data based on the signals from the respiration sensor in real time without user intervention.

24. The method of claim 19, further comprising determining when a patient's heart is in at least one of a systolic phase and a diastolic phase.

25. The method of claim 19, further comprising identifying a first interior wall and a second interior wall of a heart muscle; and determining a distance between the first interior wall and the second interior wall of the heart muscle by analyzing the distance between pixels in each column of an image.

26. The method of claim 19, wherein the alert indicates at least one of a patient condition or a problem detecting echo signals.

27. The method of claim 19, wherein identifying the endocardial border further comprises suppling the ultrasound image data to a trained neural network, wherein training the trained neural network comprises:

supplying a plurality of ultrasound test images having identifying features;

acquiring data from the ultrasound test image; and determining a plurality of filter weights and bias values.

* * * * *